(12) United States Patent
Wijay et al.

(10) Patent No.: US 6,997,903 B2
(45) Date of Patent: Feb. 14, 2006

(54) LOCAL DRUG DELIVERY CATHETER

(76) Inventors: Bandula Wijay, 1903 Carriage Creek Dr., Friendswood, TX (US) 77546; Paolo Angelini, 1970 Vermont St., Houston, TX (US) 77019

(*) Notice: Subject to any disclaimer, the term of this patent is extended or adjusted under 35 U.S.C. 154(b) by 327 days.

(21) Appl. No.: 10/360,803

(22) Filed: Feb. 10, 2003

(65) Prior Publication Data

US 2005/0033236 A1 Feb. 10, 2005

(51) Int. Cl.
*A61M 5/00* (2006.01)

(52) U.S. Cl. ...................................................... 604/117
(58) Field of Classification Search ................ 604/117, 604/21, 105–109, 272, 164.01, 164.09
See application file for complete search history.

(56) References Cited

U.S. PATENT DOCUMENTS

| | | | | |
|---|---|---|---|---|
| 5,354,271 A | * | 10/1994 | Voda ........................... | 604/539 |
| 5,354,279 A | * | 10/1994 | Hofling ................. | 604/164.12 |
| 5,364,373 A | * | 11/1994 | Waskonig et al. ........... | 604/272 |
| 5,536,267 A | * | 7/1996 | Edwards et al. ............... | 606/41 |
| 5,542,915 A | * | 8/1996 | Edwards et al. ............... | 604/22 |
| 5,542,916 A | * | 8/1996 | Hirsch et al. .................. | 604/22 |
| 5,792,099 A | * | 8/1998 | DeCamp et al. ............. | 604/506 |
| 6,181,964 B1 | * | 1/2001 | Hofmann et al. .............. | 604/21 |
| 6,302,870 B1 | * | 10/2001 | Jacobsen et al. ............. | 604/272 |
| 6,423,034 B1 | * | 7/2002 | Scarfone et al. ............. | 604/117 |
| 6,425,887 B1 | * | 7/2002 | McGuckin et al. .......... | 604/272 |
| 6,730,061 B1 | * | 5/2004 | Cuschieri et al. ............ | 604/158 |
| 2004/0167574 A1 | * | 8/2004 | Kuyava et al. .............. | 606/224 |

\* cited by examiner

*Primary Examiner*—Sharon Kennedy
(74) *Attorney, Agent, or Firm*—Kajane McManus

(57) ABSTRACT

The present invention uses several innovative means in order to effectively puncture the intimal wall of blood vessels reliably and controllably. The total penetration of the needle is controlled by the height of the needle projecting from its base and the degree of penetration is controlled by the use of "cam" or similar means or mechanisms that moves the base containing the needles.

23 Claims, 9 Drawing Sheets

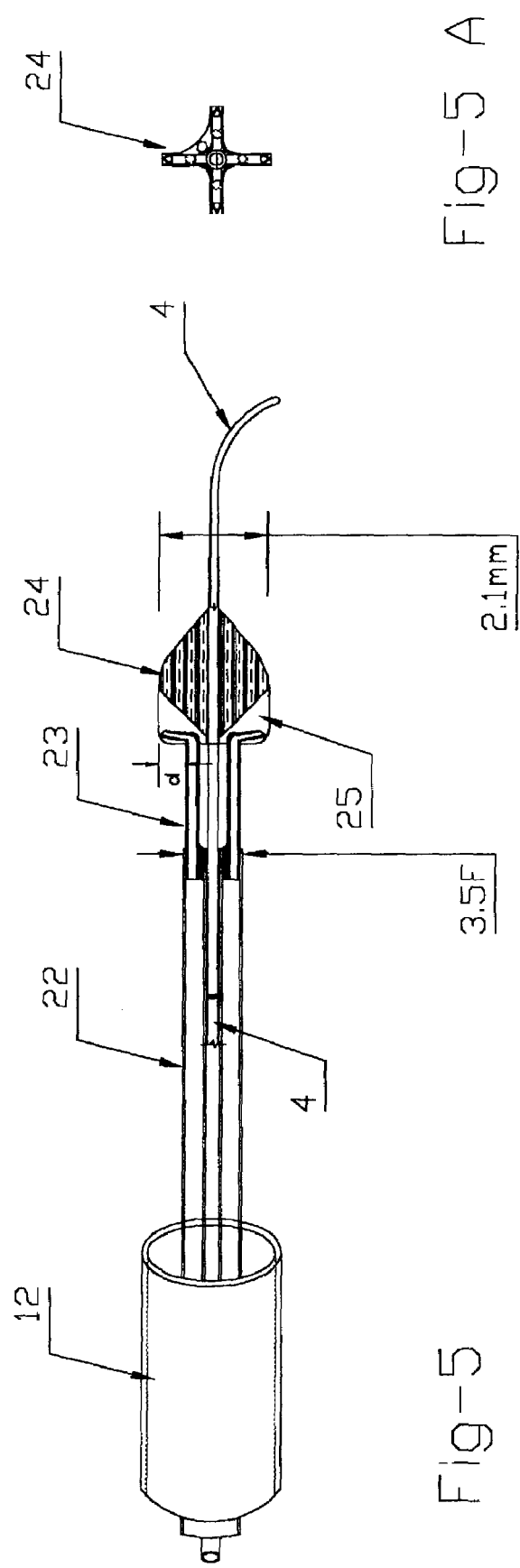

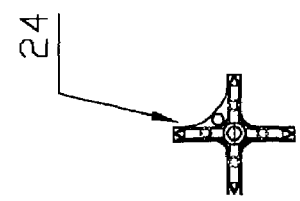
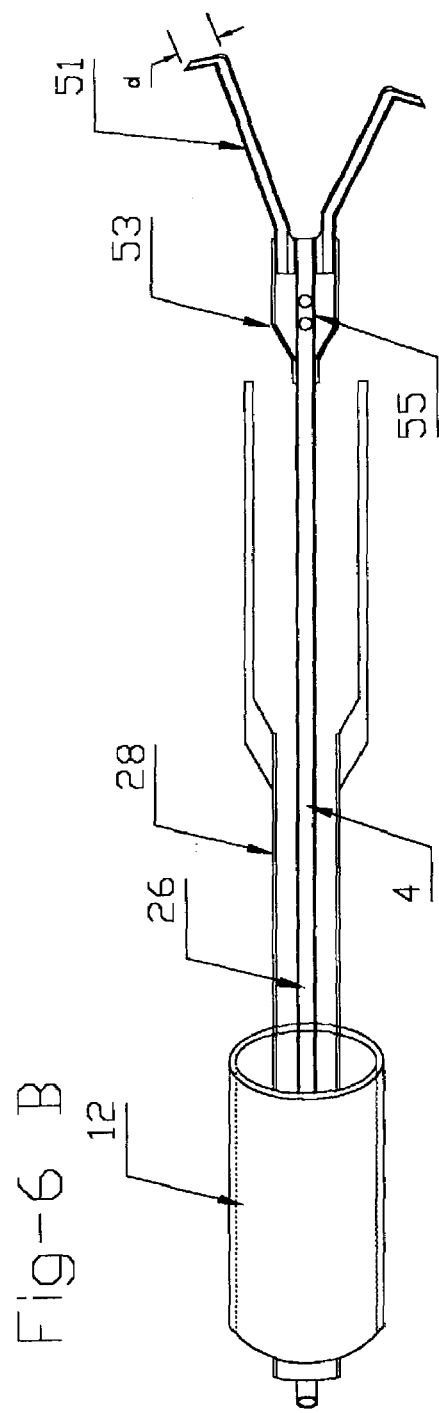
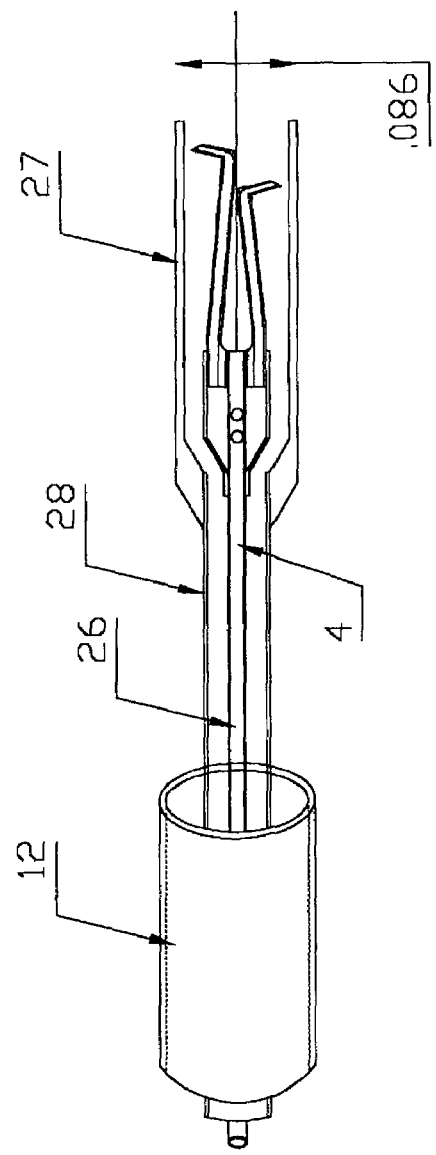

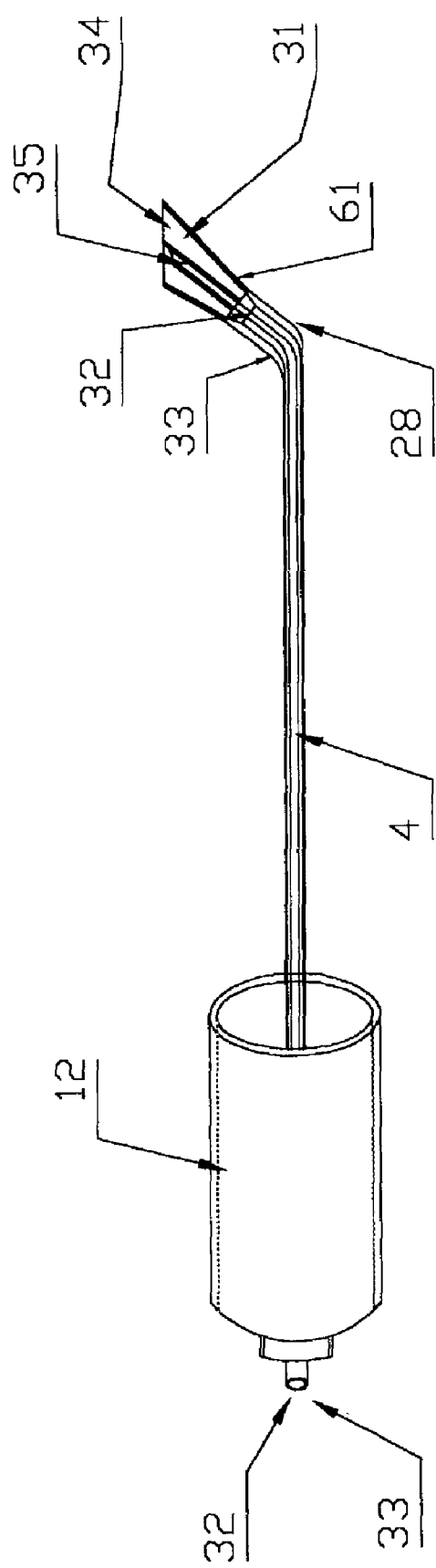

LOCAL DRUG DELIVERY CATHETER

FIELD OF THE INVENTION

The present invention relates to a method of treating tissue in a body cavity with pharmaceutical drugs or other biological techniques (like gene therapy) with the aim of realizing topical treatment as opposed to systemic treatment.

BACKGROUND OF THE INVENTION

Several medical conditions could potentially be treated more effectively by local administration of therapeutic agents. Recent Studies of the biology of arterial wall have clarified the nature of several localized pathologic changes in the intima, which could be treated effectively with local administration of variety of pharmacologic agents, for example:
 the vulnerable plaque (an atherosclerotic lesion, with high probability of rapid evolution into total occlusion, resulting in dependent tissue death), and
 the restenosis lesions (the fibro cellular proliferative response to the trauma caused by angioplasty interventions onto the vascular wall, leading to recurrent blockage of treated vessel).

Active biological processes in a localizable segment of the circulation can potentially be addressed by local administration of active pharmacologic agents more effectively than by systemic administration route. Both the tissue concentration that can be reached by local delivery and the avoidance of systemic toxicity, besides the diminished dose and cost of the active drug and quickness of its effect, all play in favor of a local administration.

Several alternative methods of local administration of drugs into the desired arterial wall have been developed and tested, namely:
 Endoluminal injection. Catheters have been devised that could obviate to the ineffectiveness of just endo-luminal infusion, while the blood circulation is maintained like temporary double balloon catheter realizing the isolation of the target vascular segment; side-holes injection through especially designed balloons (leaky balloons) or coiled tubing; needle-balloons that are inflated by the same liquid/pressure that is used to inject the active ingredient by the use of communicating needles; and others.

Klein et al. in U.S. Pat. No. 5,810,767 describe one such device where network of tubules attached onto an angioplasty type balloon. The tiny holes in the tubular network would carry the drug to the target region for drug therapy. This type of system obviously blocks the flow of blood distal to the target region and therefore can cause major problems to the patient due to ischemic manifestations.

Hanson et al. in U.S. Pat. No. 5,985,307 also describe a means to deliver drugs by binding the drug to a balloon like device which when inflated or located in the target area will allow the drug to diffuse into the vessel wall, also requiring the stoppage of the flow of fluids in the lumen.

Reed et al. in U.S. Pat. No. 6,97,013 B1, describe a balloon like device containing an array of needles that are affixed to the surface of the balloon. When the balloon is inflated, the needles will puncture into the vessel wall and the pharmacological agents are injected into the wall using the fluid agent to inflate the balloon. These devices are very bulky and are difficult to manipulate into small arteries of the heart. They need to be collapsed when the device is moved within the vessels and the procedure is very cumbersome. And if the device is not collapsed when it is advanced or withdrawn, the device can cause substantial damage to the vessel wall.

Young et al. in U.S. Pat. No. 5,788,673 describe a syringe device for controlling the rate of drug infusion systemically but provides no means to inject the drugs into the vessel wall.

Harrison et al. in U.S. Pat. No. 5,554,119, also describe a balloon like tubular device having tiny holes that would allow the infusion of the pharmacologic agents into the lumen of the vessel. Here again, the drug is easily washed away by the blood stream before it can get diffused into the vessel wall. These devices also tend to be bulky and are quite ineffective in getting the drugs into the luminal wall.

Levy et al. in U.S. Pat. No. 5,833,658 describe another balloon type device where a collar of the balloon allows flooding the pharmacologic or other agents in a vascular segment, where they can diffuse into the vessel wall. Again these types of devices occlude the flow of blood in the lumen during such procedures, which often require long periods for the diffusion of the drugs. As such they are highly ineffective. Schweich et al. in U.S. Pat. No. 5,558,642 describes a similar concept.

Schreiner in U.S. Pat. No. 5,904,670 describes a device that expands once deployed in the vessel due to shape memory characteristics. The device contains needles that can puncture into the vessel wall. While this device allows blood flow during the procedure as compared to other devices that contain a balloon, these wire cages are very cumbersome to use and the orientation of the needles is difficult to maintain, in a biological environment, where often the vessels are tortuous and non linear. Also the push-pull mechanisms that drive the needle assemblies often do not provide sufficient puncture force to puncture the intimal layers and are highly ineffective.

Jacobsen et al. describe a device in their U.S. Pat. No. 6,302,870 that has a group of retractable needles that can be made to project out of a catheter having collars to stop the penetration of the needle. The disadvantages of this design are that often it is impractical to slide a group of tubes with a small catheter tube whose overall diameter is less than 1.5 mm and it is also impractical to be able to stop the penetration of a needle with the use of a tiny needle using a collar whose diameter is only slightly larger than the needle itself. Jacobsen et al. also describe an apparatus in which the needles protrude out of a tube by the use of a twisting motion, however in order to obtain sufficient outward movement, the enclosed length has to be fairly large making the tube diameter very large causing the blockage of the lumen and making the device bulky. Additionally, there is no means to control the depth of penetration of the needles into the vessel wall.

Others, such as Haim, U.S. Pat. No. 6,254,573, on the other hand, have developed various means of injecting the drug to the wall of the blood vessel using metallic and non-metallic needles of various sizes and shapes. Although this method does not necessarily block the blood flow to the organ, actually constructing such a device that can accomplish this objective, is not easily done. The metallic "needles" are stiff and difficult to manage and the actual penetration of the needle into the vessel wall cannot be easily controlled. On the other hand "needles" made from plastics and other non-metallic materials often do not have sufficient strength and orientation to penetrate the vessel wall adequately. Any device containing a metallic needle, however small in diameter, tends to make the catheter stiff and not tractable, hence, clinically unusable.

Glines et.al. U.S. Pat. No. 6,183,444, have developed "Drug Delivery Module"—type system having a needle attached to a reservoir that is delivered using an endoscope or a catheter. Ahem et.al. U.S. Pat. No. 6,251,418 suggests a method of implanting pellets containing the drug in the myocardial tissue.

Still other inventors, such as Ungs, U.S. Pat. No. 6,149,641, have devised other means such as impregnating the drug into a carrier medium or using a porous balloon where by the drug bleeds out of the porous balloon. Winkler et.al. U.S. Pat. No. 6,200,257 discuss other methods such as a drug, placed in a hydrophilic medium, which is bonded on to the outside surface of a delivery device such as a balloon catheter or stent. Such placement of the drug can vary from just a physical mix to a covalent bond to the hydro-gel itself.

Special devices have been designed in order to access percutaneously the pericardium and then to deliver pharmacologic agents in the pericardial cavity, which is in close contact with the sub-epericardial coronary arteries. None of the above methods or devices, known as pericardial injection, have achieved clinical acceptance.

Igo et al. in U.S. Pat. No. 5,643,895, describes a method for injecting various liquid agents into the pericardium however such methods have very little chance of providing the correct amount of the agent into the target area to be effective, since they depend on diffusion in a large pericardial cavity where fluid is continuously produced and absorbed.

Recently, the technology has been perfected to cover vascular stents (metallic endovascular prosthesis) with special coatings, able to carry and then deliver (small) doses of drugs. Cordis/Johnson & Johnson produce a stent featuring polymer coating carrying small quantities of sirolimus, an anti-proliferative drug. Specifically, such stents are been evaluated to treat or prevent restenosis in stents used for coronary angioplasty. Several drugs and genetically engineered products (potentially, also virus-mediated nuclear transfusion of altered DNA material) are being tested for local delivery. The following intrinsic features potentially limit the coated/medicated stent technology: They need to be developed as a unit of stent/coating/drug, in a complex and expensive process; medicated stents provide limited amount of drugs; medicated stents can only deliver the drugs over a limited time, possibly by chemical gradient migration, or diffusion at the external wall of the stent; the active principle may have variable migration capacity, depending on the arterial wall anatomic features (fibrotic capsule, cholesterol or calcium deposits) or cellular composition (especially, concentration of macrophages); and the necessary utilization of stents, to carry the active drugs. Such active drugs may be more effective (and economical) in the absence of a stent. In the case of in-stent restenosis (recurrent obstruction, inside a previously installed stent), the use of stent inside prior stents increases the probability of new recurrence of obstruction. Additionally, it is likely that many lesions commonly treated at the present time with a stent without drug coating, may have a better and more economical result by use of stent alone and balloon angioplasty when accompanied by effective anti-proliferative medication.

For all these reasons it is believed that a specially designed device, that can reliably inject, subintimally, adequate amounts of pharmacologic agents, could improve the results of angioplasty, while limiting the cost of the intervention. It must be noted that, the absolute amount of scar tissue caused by stents is much larger than the scarring caused by stand-alone balloon angioplasty. It is the larger inner lumen that can be generally achieved with stents that can compensate for the increased scarring.

SUMMARY OF THE INVENTION

The present invention is aimed at making a device that is quite simple to produce while effective for the intend purpose. Injecting the drug into the vessel wall is more effective than the transfer of the drug from the vessel lumen by means of diffusion. While "needle" methods of injecting the drug are conceptually desirable, the prior art devices have shortcomings that prevent them from achieving their desired purpose.

Additionally other body cavities or tubes may require similar technology for local pharmacological intervention (like the bile duct, bronchi, urethra, ureter, where both scar tissue or neoplastic growths could be addressed by such means).

The present invention uses several innovative means in order to effectively puncture the intimal wall of blood vessels reliably and controllably. The total penetration of the needle is controlled by the height of the needle projecting from its base and the degree of penetration is controlled by the use of "cam" or similar means or mechanisms that moves the base containing the needles.

This method has substantial advantages over the methods where the needle has been equipped with collars and natural spring actions or shape memory actions to make the penetration into the vessel wall. Springs are not reliable means to control the force required for penetration and the same is true for the force derived by shape memory means.

The present invention contains a distal segment attached to a proximal delivery catheter, where several sharp and thin needles are provided and kept in an enclosure, until they can be moved out controllably when actuated from the proximal end of the catheter, either by turning a knob or moving a cam type mechanism. Until the needles are moved out of the cage, the needles are safely harbored and cannot cause any damage to the vessels during advancing or retracting of the device. The design of the cage is such that the movement of the tip of the catheter in the vessel will not cause vascular damage. As such the cage is preferably oblong with smooth surfaces, which is advanced over a guide wire. Once the needles are projected from the device the penetration is limited by the amount the needle can project from its base.

The needle advancing mechanism can be spring loaded with stops to control the degree of projection, and has a feature allowing immediate retrieval when the needle is withdrawn. Sequentially, multiple injections in a target region can be accomplished by slowly withdrawing the catheter while alternatively pressing and releasing the knob responsible for injecting/retrieving the needles. By so doing, a vascular segment 2–3 cm long can be treated within 5–10 minutes or less. During this process not only the pharmacological agents in liquid form are released, but also pharmacological agents, which are prepackaged in micro-capsules, can be injected into the vessel wall or the underlying tissue to be released over time. In this case the drug can be either pre-mixed into a solid "ball" of biodegradable materials or encapsulated in a thin coat, which is absorbed into the tissue releasing the active drug.

The cage itself is a low profile structure that permits blood flow before and during the injection phase.

DETAILED DESCRIPTION OF THE DRAWINGS

FIGS. 5 and 5A are an alternative embodiment to FIG. 4;

FIGS. 6A–6C show a sheath holding and releasing the needles;

FIG. 8 shows an alternative embodiment using vacuum to hold a housing to the tissue as pressure is used to inject drugs.

DETAILED DESCRIPTION OF THE PREFERRED EMBODIMENT

The object of this invention is to develop a simple and effective device for injecting various anti-proliferative and other pharmacological agents into a target area of the body cavity in an even manner. The preferred embodiment comprises a delivery catheter, which is a slender tube or catheter typically 30–150 cm long to reach different body cavities, with controlling means located at its proximal end and the drug delivery module located at its distal end. A lumen is provided to enable the catheter to be advanced over a guide wire whenever required, as is in normal catheterization procedures.

Figure 1:
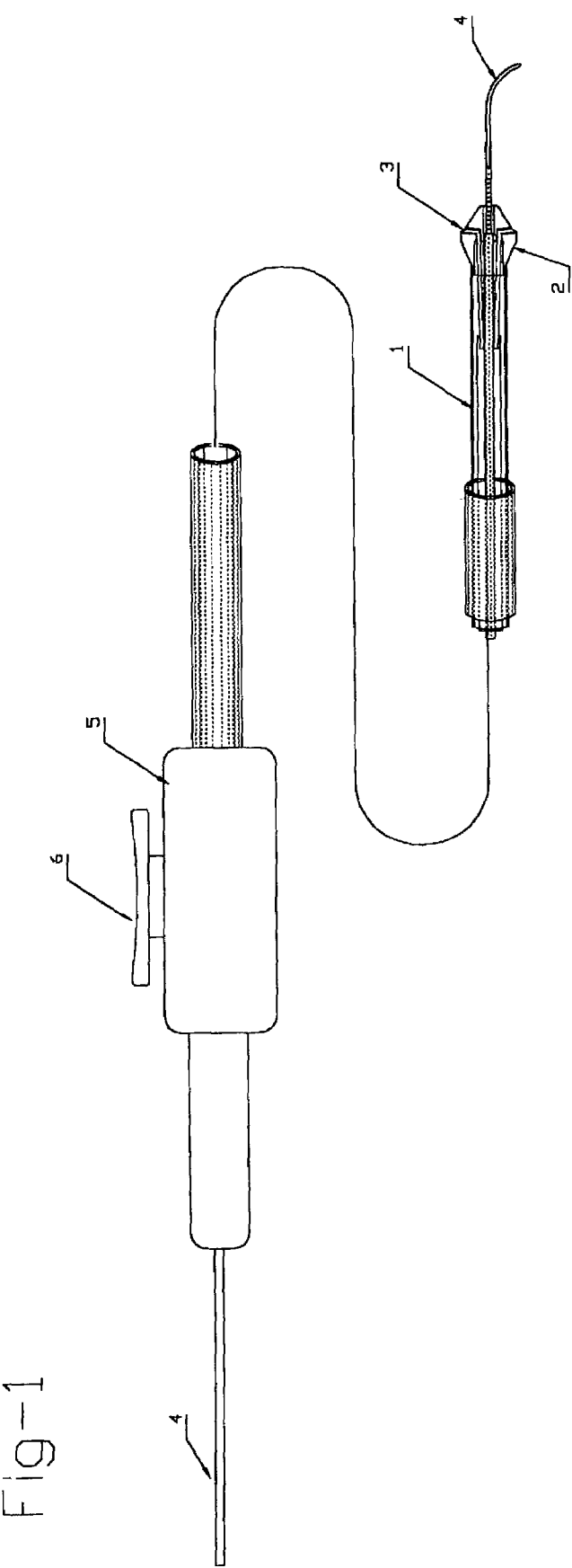
FIG. 1 shows one embodiment with the needles retracted.

A typical embodiment of such is achieved by the catheter of FIG. 1. This device has a distal end containing an injection head 2, which carries a plurality of needles attached to at least one communicating channel that extends through the catheter body 1 to the proximal end 5 that contains the needle driving mechanism having a needle-driving control unit or knob 6. This device can be advanced into the target area over a guide wire 4 for which a lumen has been provided therein. The injection head contains the retractable needles 3 that project out when activated but otherwise stay within the injection head. The injection head 2 can be spherical, elliptical or wing shaped as shown in FIG. 6 depending on the application of the device depending on whether there is fluid flow (such as blood flow) in the lumen or cavity it is used in. Other shapes may be used.

Figure 2:
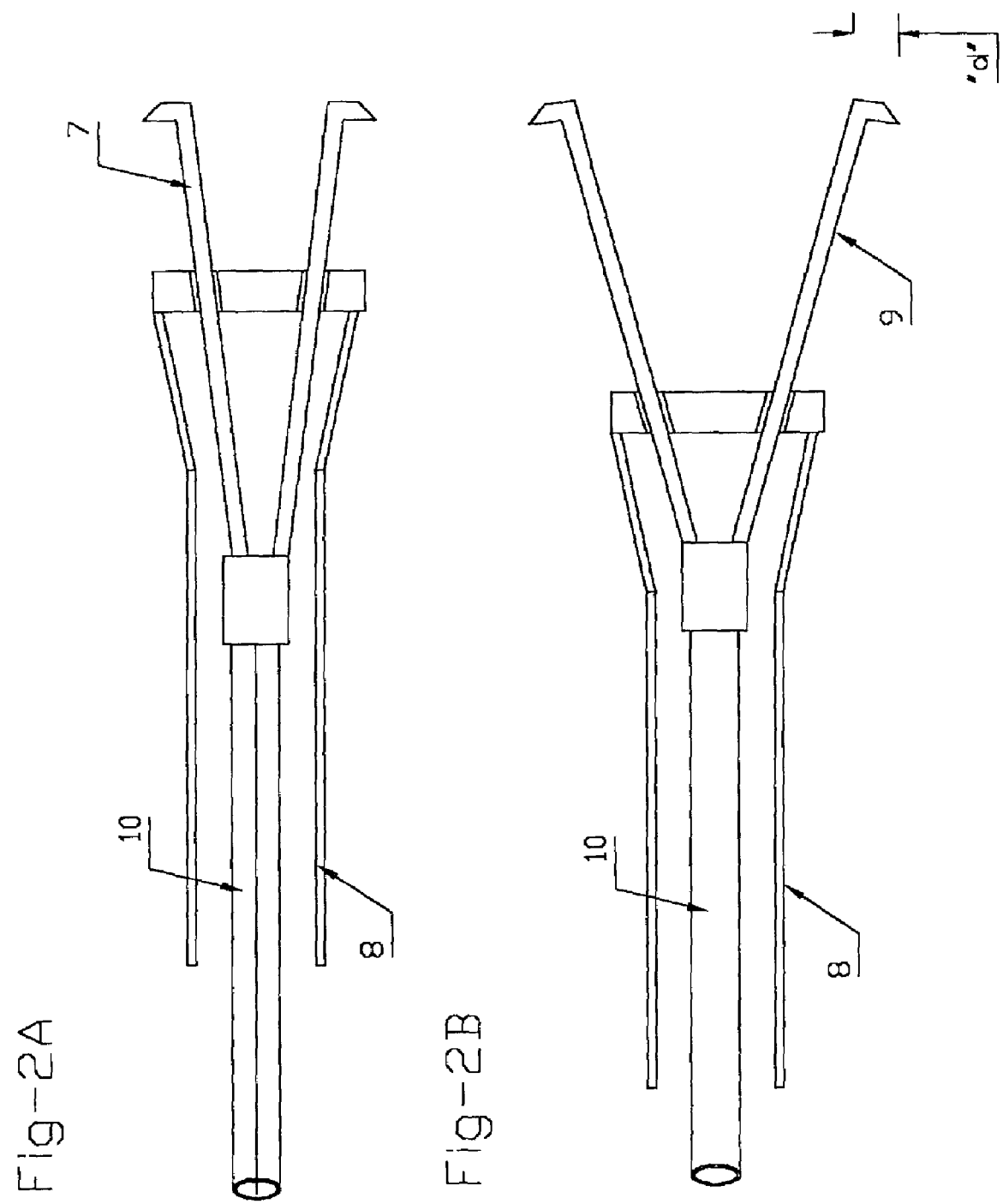
FIGS. 2A and 2B show an alternative embodiment as the needles are being extended.

The general principle is shown in FIG. 2. The needles 7 are designed with a nearly 90-degree angle at the tip (other angles can also be used depending on the design of the device and the application) and the height of the needle above the base of the needle is fixed (height "d") and controlled and predetermined. In order to have different degrees of penetration, in different cavities, it is safe to predetermine this height and use a device specific for the need. For example a small artery with a wall thickness of 2 mm, the needle height "d" can be 1.5 mm while an artery with a wall thickness of 3 mm can use a needle with needle height "d" of 2 mm. As shown in FIG. 2(B) the needles project outward when the outer casing or sheath is slid proximally. The geometrical fixation of the slide head 8 controllably moves the needles positively outwards without having to depend on spring action or shape memory action. When the slide head 8 is moved distally, the needles retract inwardly away from the wall of the artery and into the injection head 2. The penetration is controlled by the height "d" of the needle protrusion, whereby when the shank 9 or the body of the needle rests against the vessel or luminal wall no further penetration is possible even when additional force is applied to the needle assembly. When not projecting, the needles are housed within the injection head 20 (see FIG. 3) or are up against the slide head 8 in such a way not to cause any abrasion of the intimal wall during advancement or manipulation of the catheter.

The basic concept is to move the needles outward using a cam slider mechanism located in the handle at proximal end 5 and actuated by a knob 6. Limiting the penetration of the tissue by the needle is accomplished by limiting the projected height of the needle above its base. Several alternative ways of achieving this goal will now be described.

Figure 3:
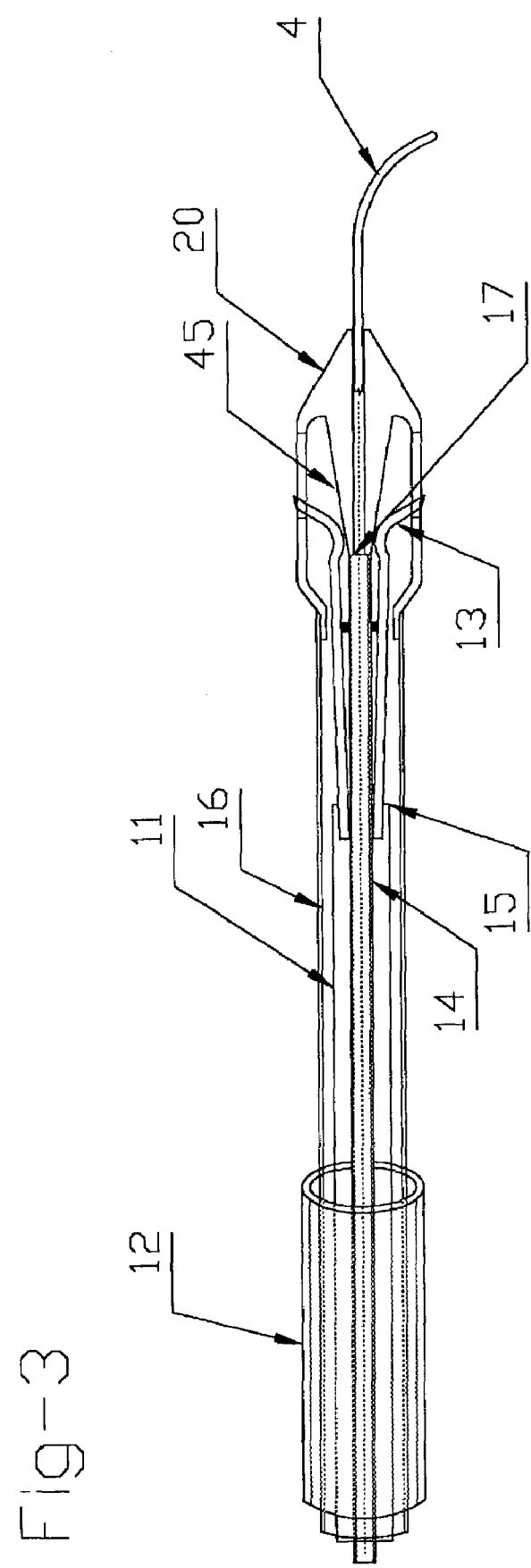
FIG. 3 is an alternative embodiment with the needles in a cage.

FIG. 3 describes one situation where the needles are safely housed within the injection head 20. The device 11 in FIG. 3 is advanced into target area through a guiding catheter 12 and over a guide wire 4. The device 11 consists of an inner tube assembly to which the needles 13 are attached in fluid communication with an inner tube assembly 14 and 15. When the outer casing 16 is moved backwards (proximally) the needles 13 will move out of the injection head and will be available to inject medications into the vessel wall. And when the outer casing 16 is moved distally the needles retract into the cage 20 completely enclosing the needles in the injection head. This is accomplished by actuating the cam 45 inside the injection head 20.

Figure 4:
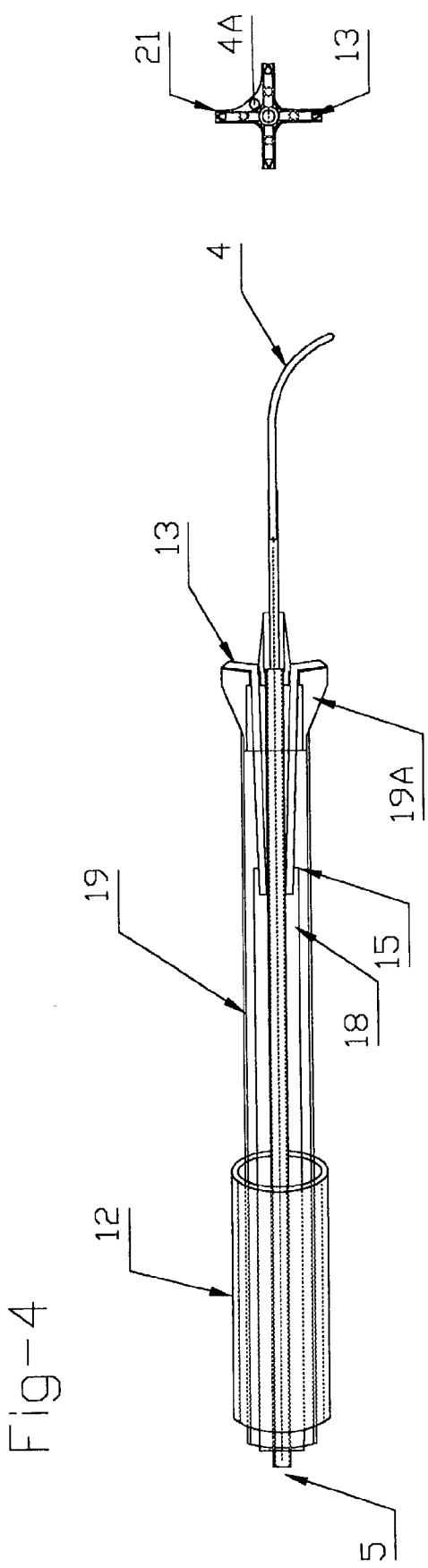
FIG. 4 shows a moving wedge forcing out the needles.

Alternatively, as shown in FIG. 4, the needles 13 are attached to one tube 15 that extends along the length of the catheter to the proximal end 5 and to the drug source. The injection head 19A is attached to tube 19 that continues along the catheter to the proximal end 6. The through lumen 14 permits a guide wire 47 to be advanced through the catheter, enabling the positioning of the catheter over the guide wire 47 in the target vessel segment. A lumen 4A provided in the injection head 19A will also permit the catheter to be advanced to the target area. This type of design will enable the device to be exchanged without having to remove the guide wire 47, which is left in place to complete an angioplasty procedure (balloon and/or stent placement). The needles 13 in this design abut the injection head 19A until it is moved proximally with respect to tube 15. A spring loading mechanism (not shown) provided in the proximal end 5, maintains the needles 13 in the retracted position at all times.

The needles 13 are connected to tube 15, which is more or less central, and preferably metallic. The tube 19 is moved forward and backward by manipulating the knob 6 in the proximal end 5, which causes the needles to expand and retract from the injection head.

In yet another configuration, as shown in FIG. 5, needles 49 move outward by using an olive-like member 24 attached to inner tube 30. The pressure can be controlled by the degree to which the olive-like member 24 is retracted into the needles 49 and the depth of penetration is controlled by the height "d" of the needles 49 as has been described earlier. As shown in FIG. 5, a plurality of needles 49 can be provided in order to inject the medications uniformly. When the needles 49 are not projected outwards, they are maintained within the housing 25. The housing 25 may have different variations in its design; especially its distal end may be similar to the injections heads shown in FIG. 3 and FIG. 4.

In each case the movement is accomplished by means of either a tapered cam 20 (FIG. 3) or the cam with "holes" as in 21 (FIG. 4), which may or may not be a part of the cage. When the cam is moved proximally the needles project out and when the cam is moved distally the needles retract.

Figure 7A:
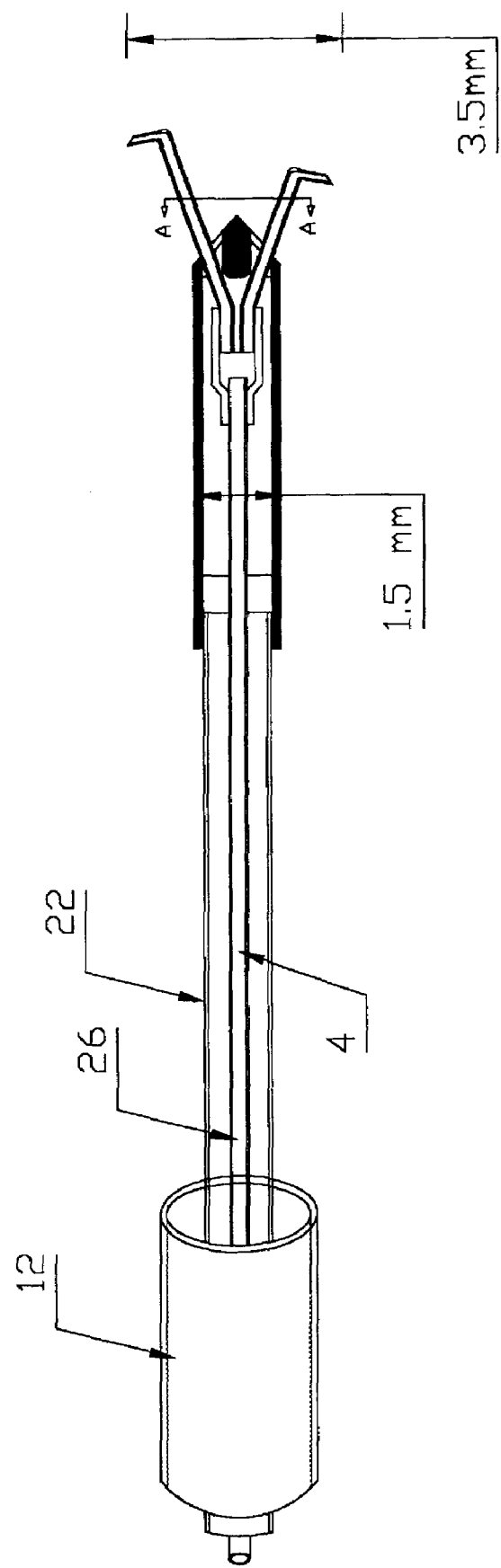
FIGS. 7A–7D show an alternative embodiment where the tip aids in pushing out the needles.
Figure 7B:
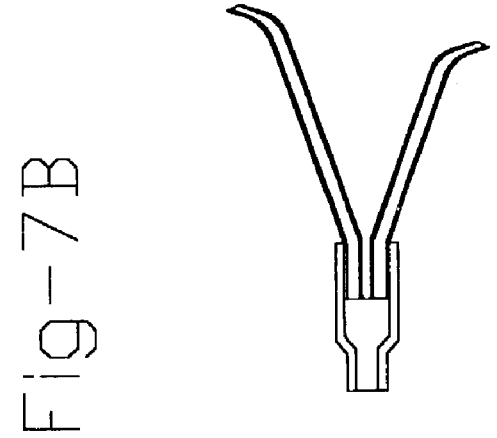

Still another variation of the invention is shown in FIG. 6A and FIG. 6B. In this design the needles 51 are attached to an inner tube 26, which is in fluid communication with the injection head 53 and the injection needles 51. The tube 26 is a flexible plastic tube made from such materials like nylon, polyethylene, polyurethane, polyimide etc. and may contain a spring coil or a stylet 55 at least for a portion of its length to provide resistance to kinking as well as to enhance pushability of this inner member. The outer sheath contains a housing 27, made from metal or plastic to maintain the needle assembly enclosed during the advancement of the catheter to the arteries of the heart or other parts of the human body. An additional lumen 28 is provided on the outer or inner wall of the sheath 27. The outer sheath 27 can also be made from a single piece. When the inner tube member 26 is pushed out or when the sheath 27 is pulled back the needles 51 will spring out as shown in FIG. 6B. The needles 51 have an angular shape at their ends causing the needles depth of penetration to the height "d" (as discussed before in FIG. 2B) of the needle above its base. The direction of the needle tip can be projecting perpendicular (FIG. 6B) to the axis of the artery, projecting forward (FIG. 7B) or projecting backwards (FIG. 7A), depending on the actual action imposed on the device to incur penetration of the needles into the artery.

Figure 7C:
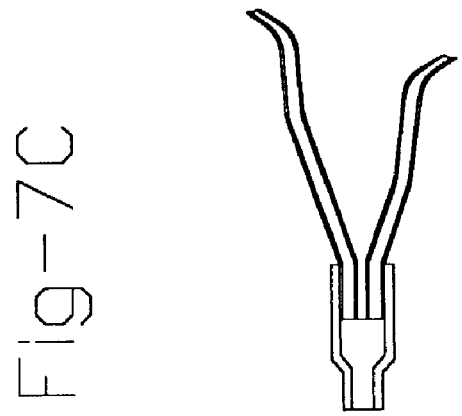
Figure 7D:
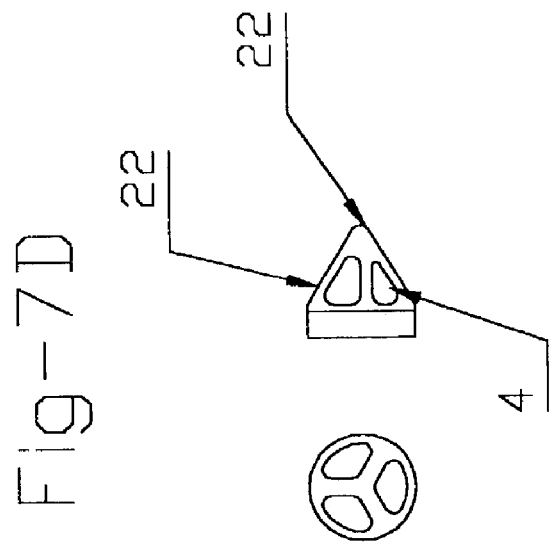

The distal end of the sheath may also contain a diverting mechanism as shown in FIG. 7D. This structure generally has a bullet shaped end, 53 for ease of entry to tight lesions. The structure has a head, 55 divided into three (for accommodating three needles) As the sheath is moved back, the head will push against the needles to force them to positively deflect it outwards through the holes, 57 located in the head, 55 in addition to their normal deflection due to their spring action making a positive and controlled deflection. The diameter of the holes 57 are considerably larger than the needle diameter to minimize any friction which would be the case if the clearance between the needles and the hole is very small to help the penetration of the tissue where such additional force of penetration is required.

The needle assembly in FIG. 6A shows the arrangement of the needles 51 which have different lengths to be staggered so that when the needles 51 are collapsed inside the cage each needle will not interfere with the other needle. This allows conserving space when the needles are folded into the sheath.

FIG. 7C shows that the needles have an additional bend to provide a land area 59, so that when the needle is deflected the land area 59 will help the needle to rest on the tissue preventing over penetration of the needle as previously discussed.

Depending on the size of the catheter and the location where drug therapy is needed, the number of needles can be 2 or more. Typically 2–6 needles are sufficient to inject a pharmacological agent uniformly into the vessel wall.

In another version of the present invention, drugs in its liquid form or encapsulated drugs can be implanted into the heart muscle or the walls of the coronary artery using the device shown in FIG. 8. This device contains a small suction cup 31 made of metal or plastic with numerous holes 34. The application of suction to a lumen connected to these suction holes will hold the cup firmly against the wall of the vessel of the heart. Once this is achieved the needle 35 can be advanced to a stop 61 to penetrate the wall and the drugs can be delivered either under pressure or the encapsulated solid form pharmaceuticals can be delivered using a push rod mechanism. The neck section 28 is bent and is made of flexible material so as to adjust to the required angle. The drugs are delivered by applying pressure to lumen 32 and the suction cup is held in place by applying suction to lumen 33.

The foregoing disclosure and description of the invention are illustrative and explanatory thereof, and various changes in the size, shape and materials, as well as in the details of the illustrated construction, may be made without departing from the spirit of the invention.

We claim:

1. A drug injection device for delivering at least one pharmacological agent in a body cavity, comprising:
   a body having a proximal and distal end;
   at least one needle mounted for movement with respect to said body for selective movement away from said body, said needle having at least one bend adjacent a distal end thereof and located outside of said body when it limits penetration of said needle into a wall defining a body cavity.

2. The device of claim 1, wherein:
   said at least one needle comprises a plurality of needles of different lengths.

3. The device of claim 2, wherein:
   said needle is made from one of stainless steel and a shape memory alloy and is one of round and rectangular in cross-section.

4. The device of claim 1, wherein:
   said bend defines an included angle that is one of acute, right, or obtuse.

5. The device of claim 1, wherein:
   said needle is housed within said body for delivery to the cavity.

6. The device of claim 5, wherein:
   said body comprises a sheath to cover said distal end of said needle for delivery to the body cavity, whereupon relative motion between said sheath and said needle, a stored force on said needle is released to drive said distal end up to said bend into the wall defining the body cavity.

7. The device of claim 1, wherein:
   said at least one bend comprises at least a proximal and a distal bend, said distal end, up to said distal bend, penetrating the wall defining the body cavity and said second bend defining a segment of said needle between said bends that contacts the wall that defines the body cavity.

8. The device of claim 7, wherein:
   said proximal bend biases said segment of said needle toward the wall that defines the body cavity.

9. The device of claim 1, wherein:
   said body comprises a lumen to allow said body to be advanced over a guide wire and to be removed while leaving the guide wire in place.

10. The device of claim 9, further comprising:
    one of a sheath and a guiding catheter through which said body can be guided to the body cavity.

11. A drug injection device for delivering at least one pharmacological agent in a body cavity, comprising:
    a body having a proximal and distal end;
    at least one needle mounted for movement with respect to said body for selective movement away from said body, said needle having at least one bend adjacent a distal end thereof that limits its penetration into a wall defining a body cavity;
    said distal end of said needle is cammed away from said body.

12. The device of claim 11, wherein:
    said body comprising a longitudinal axis and an opening oriented askew to said longitudinal axis, said needle extending through said opening, whereupon relative movement between said body and said needle, said distal end of said needle is selectively extended and retracted with respect to the wall defining the body cavity.

13. The device of claim 11, wherein:
said camming occurs by relative movement between a tapered surface of said body and said needle.

14. The device of claim 13, wherein:
said tapered surface contacts said needle adjacent said bend.

15. The device of claim 13, wherein:
said needle comprises a proximate end and said tapered surface contacts said needle adjacent said proximate end.

16. The device of claim 13, wherein:
camming of said distal end of said needle away from said body is accomplished by said tapered surface upon relative movement in a first direction, whereupon reversal of said relative movement, said distal segment retracts due to one of a stored force therein and shape memory.

17. A method of delivering a drug to a body cavity wall, comprising:
delivering a catheter body into the cavity;
configuring at least one delivery needle with at least one bend;
using said bend when located outside said catheter to limit penetration of the distal end of said needle into the cavity wall;
delivering the drug through said needle.

18. The method of claim 17, comprising:
delivering a microencapsulated drug through said needle;
releasing the drug over an interval of time into the cavity wall.

19. The method of claim 17, comprising:
implanting an anti-proliferative drug through said needle;
reducing the proliferation of scar tissue or restenosis with said anti-proliferative drug.

20. The method of claim 17, comprising:
implanting different pharmacological agents through said needle.

21. The method of claim 17, comprising:
delivering said catheter into any one of an artery, the urethra, a bile duct and the esophagus.

22. The method of claim 17, comprising:
moving the catheter to inject a drug into different lesions in a single insertion.

23. The method of claim 17, comprising:
pulling a vacuum on an opening in the catheter;
retaining the catheter body to the cavity wall;
extending said needle through said opening in the catheter.

* * * * *